United States Patent [19]

Habermann

[11] 4,153,581

[45] May 8, 1979

[54] METHOD OF PRODUCING AMINES FROM ALCOHOLS, ALDEHYDES, KETONES AND MIXTURES THEREOF

[75] Inventor: Clarence E. Habermann, Midland, Mich.

[73] Assignee: The Dow Chemical Company, Midland, Mich.

[21] Appl. No.: 829,758

[22] Filed: Sep. 1, 1977

[51] Int. Cl.$^2$ .................. B01J 23/40; B01J 23/74
[52] U.S. Cl. .................. 252/472; 260/585 B; 260/585 C; 252/457; 252/459; 252/463; 252/466 J; 252/473; 252/474
[58] Field of Search .......... 260/585 B, 585 C; 252/472, 473, 474, 457, 459, 463, 466 J

[56] References Cited

U.S. PATENT DOCUMENTS

| | | |
|---|---|---|
| 3,268,588 | 8/1966 | Horlenko et al. .......... 260/585 B |
| 3,270,059 | 8/1966 | Winderl et al. .......... 260/585 B |
| 3,346,640 | 10/1967 | Guyer et al. .......... 260/585 C X |
| 3,520,933 | 7/1970 | Adam et al. .......... 260/585 C |

*Primary Examiner*—Paul F. Shaver
*Attorney, Agent, or Firm*—G. R. Plotecher

[57] ABSTRACT

A method of producing amines, the method comprising contacting at reactive conditions at least one alcohol, aldehyde or ketone, or a mixture thereof, with an aminating agent in the presence of a catalyst, is improved by employing as the catalyst a composition comprising cobalt, copper and a third component selected from the group consisting of iron, zinc, zirconium and mixtures thereof. For example, polypropylene glycol is quantitatively aminated by contacting it with ammonia at about 175° C. and in the presence of a catalyst comprising (metal basis) 30 mole percent cobalt, 63 mole percent copper and about 7 mole percent iron.

23 Claims, No Drawings

METHOD OF PRODUCING AMINES FROM ALCOHOLS, ALDEHYDES, KETONES AND MIXTURES THEREOF

BAKCKGROUND OF THE INVENTION

1. Field of the Invention

This invention relates to an improved method of producing amines from alcohols, aldehydes, ketones and mixtures thereof. In one aspect, the invention relates to an ammonolytic method while in another aspect it relates to a catalyst useful therein.

2. Description of the Prior Art

The art is replete with catalysts useful for the ammonolysis of an alcohol, and particularly primary and secondary alcohols, to the corresponding amine. Shirley and Speranza, U.S. Pat. No. 3,128,311, teach a catalyst comprising about 50 to 90 weight percent nickel, about 10 to 50 weight percent copper and about 0.5 to 5 weight percent of an oxide selected from the class consisting of chromium oxide, titanium oxide, thorium oxide, magnesium oxide, zinc oxide and manganese oxide. Moss, U.S. Pat. No. 3,152,998, teaches a catalyst characterized by having the composition calculated in mole percent on an oxide-free basis of 60 to 85 percent nickel, 14 to 37 percent copper and 1 to 5 percent chromium. Yeakey, U.S. Pat. No. 3,654,370, teaches a similar catalyst. Zech, U.S. Pat. No. 3,347,926, teaches a catalyst containing aluminum, nickel and chromium. Boettger et al., U.S. Pat. No. 4,014,933, teach a catalyst which (calculated on the metal content of the catalyst) contains 70 to 95 weight percent of a mixture of cobalt and nickel and 5 to 30 weight percent of copper, the weight ratio of cobalt:nickel being from 4:1 to 1:4. While these and other catalysts have demonstrated ammonolytic utility, catalysts demonstrating superior ammonolytic activity are desirable for the very pragmatic reasons of economy, efficiency, convenience, etc.

SUMMARY OF THE INVENTION

According to this invention, a method of producing amines, the method comprising contacting at reactive conditions at least one alcohol with an aminating agent in the presence of an ammonolytic catalyst, is surprisingly improved by using as the catalyst a composition comprising (calculated in mole percent and on an oxide-free basis) about 20–90 percent cobalt, 8–72 percent copper and 1–16 percent of a third component selected from the group consisting of iron, zinc, zirconium and mixtures thereof. These compositions demonstrate superior ammonolytic activity thus allowing quantitative conversion of the alcohol to the corresponding amine at less rigorous method conditions. Moreover, these compositions demonstrate excellent selectivity and life.

The ammonolytic mechanism of this invention is believed to comprise:
(a) dehydrogenating the alcohol to the corresponding aldehyde or ketone;
(b) adding the aminating agent to the aldehyde or ketone to form an imine; and
(c) hydrogenating the imine to the corresponding amine.

Consequently, the catalytic compositions of this invention are also useful for the ammonolysis of aldehydes and ketones to the corresponding amines.

DETAILED DESCRIPTION OF THE INVENTION

The catalytic compositions here used are generally three-component compositions comprising (calculated in mole percent and on an oxide-free basis) about:
(1) 20 to about 90 percent cobalt;
(2) 8 to about 72 percent copper; and
(3) 1 to about 16 percent of a third component selected from the group consisting of iron, zinc, zirconium and mixtures thereof.

Compositions comprising about:
(1) 30 to about 80 percent cobalt;
(2) 15 to about 60 percent copper; and
(3) 2 to about 14 percent of the third component are preferred, with compositions comprising about:
(1) 40 to about 70 percent cobalt;
(2) 20 to about 50 percent copper; and
(3) 4 to about 12 percent of the third component especially preferred. Compositions wherein the third component comprises only iron, or only zinc or only zirconium are familiar and thus preferred to compositions wherein the third component comprises a mixture of these components. Compositions wherein the third component comprises only zirconium are particularly preferred.

These compositions can be used either unsupported or supported. Typical supports include: alumina, silica, zirconia, zircon (a mixture of zirconia and silica), magnesia, and various cation exchange resins, such as Dowex ® HCR, Dowex ® MSC-1, and Dowex ® CCR-2 (all manufactured by The Dow Chemical Company and comprising a sulfonated styrene-divinylbenzene copolymer matrix). If the composition is supported, the metal loading (on an oxide-free basis) is usually at least about 0.5 percent and preferably at least about 10 percent of the total weight (support plus composition). The maximum metal content can vary to convenience but it is generally about 50 weight percent and preferably about 20 weight percent.

The catalytic compositions of this invention are readily prepared by any number of different methods but are typically prepared by first precipitating the metal components from their salts, e.g., nitrates, chlorides, sulfates, acetates, etc., in a basic, aqueous solution, e.g., sodium or ammonium carbonate, sodium or potassium hydroxide, alkali (ne earth) metal oxalates, silicates or aluminates, etc. The metal precipitate is then washed, filtered and dried at an elevated temperature, e.g., 60° C.–180° C., and the dry precipitate is then decomposed at a temperature between about 200° C. and about 400° C. for a suitable period of time, e.g., 2 hours, to the corresponding oxides. If desired, preparation of the composition can commence with commercially available oxides rather than first preparing the oxides as here described. The resulting oxide mixture is then reduced with hydrogen, sodium borohydride, hydrazine, a reducing metal of greater oxidation potential than cobalt, carbon monoxide or some other suitable reducing agent. The degree of reduction is temperature dependent but generally, the first two components (cobalt and copper) are reduced to the active metal while the third component, i.e., zinc, iron, zirconium or a mixture thereof, remains an oxide. When this reduction is with hydrogen, a temperature between about 150° C. and about 250° C. for about 6 to 7 hours is usually adequate. The reduced catalyst is thereafter generally handled in the absence of air. If a supported catalyst is desired, the metal salts can be precipitated directly upon or with the carrier (support).

These compositions can also be prepared from suitable alloys of the three components and at least one leachable fourth component. For example, an alloy of cobalt, copper, zirconium and aluminum can be formed and subjected to caustic whereby the aluminum is leached from the alloy. The resulting Raney-like structure is then ready for use.

A catalytic amount of the composition is required for the practice of this invention. The minimum amount of catalyst required will vary with the method reagents and conditions, but a typical minimum amount is about 0.1 weight percent, and preferably about 1 weight percent, based on the weight of the starting materials. Practical considerations, such as convenience, catalyst recovery, economy, etc., are the only limitations upon the maximum amount of catalyst that can be used, although these considerations prefer a maximum of about 25 weight percent, and most preferably of about 10 weight percent.

Any alcohol that can be used in known ammonolytic methods can be used in the practice of this invention. These alcohols comprise a wide variety of hydroxy-containing materials. Representative alcohols include: primary and secondary alcohols, such as alkanols of 1 to about 18 carbon atoms, e.g., methanol, n-propanol, isopropanol, n-butanol, sec-butanol, isobutanol, pentanol, hexanol, 2-ethylhexanol, tridecanol, stearyl alcohol, etc.; cycloalkanols of 5 to 12 carbon atoms, e.g., cyclohexanol, cycloheptanol, etc.; aralkanols of 7 to about 40 carbon atoms, e.g., benzyl alcohol, 2-phenyl ethanol, etc.; polyhydric alcohols of 2 to about 15 carbon atoms, e.g., ethylene glycol, propylene glycol, 1,3-butanediol, 1,4-butanediol, 1,5-pentanediol, hexamethylene glycol, decamethylene glycol, 1,12-dihydroxyoctadecane, glycerol, etc.; polymeric polyhydric alcohols, e.g., polyvinyl alcohol; glycol ethers and polyalkylene glycol ethers, e.g., methyl glycol, ethyl glycol, butyl glycol, diethylene glycol, triethylene glycol, tetraethylene glycol, higher polyethylene glycols, dipropylene glycol, tripropylene glycol, polypropylene glycol ether, polybutylene glycol ether, etc.; aminated alcohols, such as alkanolamines, e.g., ethanolamine, propanolamine, isopropanolamine, hexanolamine, diethanolamine, diisopropanolamine, dimethylethanolamine, etc.; and aminated polyhydric alcohols and glycol ethers, e.g., aminated polyethylene glycol, etc. Other suitable hydroxycontaining compounds are disclosed in U.S. Pat. No. 3,347,926, U.S. Pat. No. 3,654,370 and U.S. Pat. No. 4,014,933.

Any aldehyde or ketone that can be produced from the dehydrogenation of the alcohols here used can also be used in the practice of this invention. Representative aldehydes include: methanal, ethanal, propanal, butanal, cyclohexanal, benzylaldehyde, and aldehydes prepared from the dehydrogenation of polyhydric alcohols, polymeric polyhydric alcohols, glycol ethers and polyalkylene glycol ethers, aminated alcohols, aminated polyhydric alcohols and glycol ethers, etc. Representative ketones include: propanone, butanone, 2-pentanone, 3-pentanone, 3-methyl-2-butanone, 1-phenyl-2-propanone, acetophenone, n-butyrophenone, benzophenone, 3-nitro-4'-methylbenzophenone and ketones prepared from the dehydrogenation of polyhydric alcohols, polymeric polyhydric alcohols, glycol ethers and polyalkylene glycol ethers, aminated alcohols, aminated polyhydric alcohols and glycol ethers, etc.

As used herein, "at least one alcohol, aldehyde or ketone, or a mixture thereof," means that these compounds can be used either singly (which is preferred), i.e., only one alcohol, only one aldehyde or only one ketone, or in a mixture comprising a combination of these compounds, e.g., a mixture of two or more alcohols, or two or more aldehydes, or two or more ketones, or of at least one alcohol and at least one aldehyde, or of at least aldehyde and at least one ketone, or of at least one alcohol and at least one ketone, or of at least one alcohol, at least one aldehyde and at least one ketone.

"Alcohol" includes those compounds containing both a hydroxy function and a carbonyl function and "aldehyde" includes those compounds without a hydroxy function but containing both an aldehyde carbonyl and a ketone carbonyl. Aldehydes are preferred to ketones and alcohols are preferred to aldehydes.

The aminating agents of this invention are ammonia or primary or secondary amines. The primary and secondary amines generally have alkyl radicals of 1 to about 12 carbon atoms or cycloalkyl radicals of 5 to 8 carbon atoms or aralkyl radicals of 7 to about 40 carbon atoms and include such compounds as: methylamine, dimethylamine, ethylamine, diethylamine, n-butylamine, sec-butylamine, isobutylamine, ethylenediamine, benzylamine, etc. Other suitable amines include cyclic amines which can contain hetero atoms other than nitrogen, such as oxygen, and these compounds include: morpholine, pyrrolidine, piperidine, piperizine, etc. When ammonia is the aminating agent, primary amines are obtained; when a primary amine is the aminating agent, secondary amines are obtained; when a secondary amine is the aminating agent, tertiary amines are obtained. These aminating agents, like the alcohols, aldehydes and ketones, can also be used either singly or in combination with one another. The former is preferred. Primary amines are preferred to secondary amines and ammonia is preferred to primary amines.

Stoichiometric amounts of alcohol and aminating agent are required for the practice of this invention. However, for reasons of convenience and efficiency it is preferable to practice this invention with a stoichiometric excess of aminating agent to alcohol. Typically, a minimum aminating agent:alcohol mole ratio of about 1:1 and preferably of about 5:1 is employed. Practical consideration, such as economy, reaction equipment, etc., are the only limitations upon the maximum said ratio but these considerations prefer a mole ratio of about 200:1 and more preferably of about 100:1. The typical aminating agent:aldehyde, ketone or mixture mole ratios are generally the same as the here recited aminating agent:alcohol mole ratios.

The method of this invention generally employs hydrogen. The amount of hydrogen employed, if employed, can vary to convenience but a typical minimum hydrogen: alcohol mole ratio is at least about 0.1:1 preferably at least about 1:1. A typical maximum mole ratio is about 50:1 and preferably about 20:1. Again, the typical hydrogen:aldehyde, ketone or mixture mole ratios are generally the same as the here recited hydrogen:alcohol mole ratios.

Although conventional method conditions can here be used, the superior catalytic activity of this invention's composition permits the ammonolytic process to proceed at lower temperatures and pressures. For example, this invention can be practiced at a temperature of at least about 75° C. although preferred reaction rates are obtained at a temperature of at least about 120° C. Pressures are of course dependent upon temperature but a minimum pressure of about 1,000 psi can be used although a minimum pressure of about 1,500 psi is preferred. Again, practical considerations are the only limitations upon the maximum temperature and pressure but a maximum temperature of about 400° C. and a maximum pressure of about 10,000 psi are preferred. A more preferred maximum temperature is about 250° C. and a more preferred maximum pressure is about 6,000 psi.

The invention can be practiced on either a continuous or batch operation, in both the liquid and gas phases, and either neat or in the presence of an inert solvent. By "inert" is meant that the solvent is essentially nonreactive with the method reagents and products at the method conditions. Exemplary solvents include tertiary alcohols, such as tertiary butanol, tertiary amylalcohol, etc.; ethers, such as diethylether, dimethylether, etc.; aliphatic and aromatic hydrocarbons, such as hexane, heptane, cyclohexane, benzene, toluene, xylene, etc.; halogenated aliphatic and aromatic hydrocarbons, such as chloroethane, dichloroethane, chlorobenzene, o-dichlorobenzene, chloroform; and nonreactive tertiary amines, such as pyridine, picoline, lutadine, etc. Moreover, this method can be practiced in either the presence or absence of water although if water is present, it is preferred that it is not present in amounts greater than about 50 weight percent of the alcohol, aldehyde, ketone or mixture.

Whether the amines produced by this invention are primary, secondary or tertiary depends not only upon the aminating agent employed, as earlier noted, but also upon the particular method conditions employed. Short contact time, e.g., between about 0.1 seconds and about 15 minutes, excess ammonia and low temperature and pressure generally favor the production of primary amines. As the aminating agent: alcohol, aldehyde, ketone or mixture mole ratio decreases and/or the temperature increases and/or the contact time increases, secondary and tertiary amines form a larger percentage of the method product. However, longer reaction time favors greater amination of the alcohol. Accordingly, by appropriate selection of aminating agent and method conditions, it is possible to influence the method product mix of primary, secondary and tertiary amines.

The following examples are illustrative of certain specific embodiments of this invention. Unless otherwise noted, all parts and percentages are by weight.

SPECIFIC EMBODIMENTS

Catalyst Preparation

The catalysts used in the following examples and controls (unless indicated otherwise) were prepared by adding a solution (0.5 molar) of the corresponding nitrates and a solution (0.5 molar) of ammonium carbonate simultaneously to a reaction flask. The pH (about 6.5) was controlled by the flow rate of the respective solutions. The resulting precipitated carbonates were washed, filtered and subsequently dried at about 60° C. The dry carbonates were then decomposed at about 250° C. for about 1 hour to the corresponding oxides. The oxides were subsequently reduced with hydrogen at a temperature of about 200° C. for about 6 hours. The reduced catalyst was then handled in the absence of air.

Procedure

Reduced catalyst (15 g) prepared as above and polypropylene glycol (15 g) of about 400 molecular weight were changed under a protective atmosphere of nitrogen to a rocking autoclave. The autoclave was then charged with ammonia (60 g) and hydrogen (500 psig) and the autoclave contents were subsequently heated for about 5 hours at about 140° C. Afterwards, the autoclave was cooled, vented and the catalyst removed by filtration. The catalyst was then washed with dry methanol and the washings combined with the remaining autoclave contents. Methanol and water were then removed from these contents by a Rinco rotary evaporator and the resulting product analyzed either by vapor phase chromatography or titration with hydrochloric acid.

EXAMPLES 1–32

The following examples were performed with catalysts prepared as above and by the procedure as above. The figures preceding each catalyst component represent that component's mole percent of the catalyst on an oxide-free basis. The figures reported at the percent amination column represent the weight percent of polypropylene glycol aminated.

| Ex | Catalyst | Amination Wt. % |
|---|---|---|
| 1 | 20-Co, 64-Cu, 16-Zn | 26 |
| 2 | 30-Co, 56-Cu, 14-Zn | 36 |
| 3 | 40-Co, 48-Cu, 12-Zn | 29 |
| 4 | 50-Co, 40-Cu, 10-Zn | 27 |
| *5 | 60-Co, 32-Cu, 8-Zn | 28 |
| 6 | 70-Co, 24-Cu, 6-Zn | 27 |
| 7 | 80-Co, 16-Cu, 4-Zn | 23 |
| 8 | 90-Co, 8-Cu, 2-Zn | 13 |
| 9 | 20-Co, 72-Cu, 8-Zr | 8-Zr |
| 10 | 30-Co, 63-Cu, 7-Zr | 46 |
| 11 | 40-Co, 54-Cu, 6-Zr | 52 |
| 12 | 50-Co, 45-Cu, 5-Zr | 53 |
| 13 | 60-Co, 36-Cu, 4-Zr | 47 |
| 14 | 70-Co, 27-Cu, 3-Zr | 45 |
| 15 | 80-Co, 18-Cu, 2-Zr | 45 |
| 16 | 90-Co, 9-Cu, 1-Zr | 27 |
| 17 | 20-Co, 64-Cu, 16-Fe | 12 |
| 18 | 30-Co, 56-Cu, 14-Fe | 20 |
| 19 | 40-Co, 48-Cu, 12-Fe | 26 |
| 20 | 50-Co, 40-Cu, 10-Fe | 33 |
| 21 | 60-Co, 32-Cu, 8-Fe | 35 |
| 22 | 70-Co, 24-Cu, 6-Fe | 28 |
| 23 | 80-Co, 16-Cu, 4-Fe | 19 |
| 24 | 90-Co, 8-Cu, 2-Fe | 31 |
| 25 | 20-Co, 72-Cu, 8-Fe | 54 |
| 26 | 30-Co, 63-Cu, 7-Fe | 60 |
| 27 | 40-Co, 54-Cu, 6-Fe | 52 |
| 28 | 50-Co, 45-Cu, 5-Fe | 55 |
| 29 | 60-Co, 36-Cu, 4-Fe | 51 |
| 30 | 70-Co, 27-Cu, 3-Fe | 35 |
| 31 | 80-Co, 18-Cu, 2-Fe | 51 |
| 32 | 90-Co, 9-Cu, 1-Fe | 51 |

*Contact time of about 6.25 hours.

EXAMPLE 33

A rocking, 300 cc autoclave was charged with monoethanolamine (20 g), ammonia (75 g), hydrogen (500 psig) and a catalytic composition (8 g) comprising cobalt (30 mole percent), copper (63 mole percent) and $Fe_2O_3$ (7 mole percent). The charged autoclave was heated to about 180° C. and held thereat for 5 hours while continually rocked. Thereafter excess ammonia was vented, the contents filtered and subsequently analyzed by gas chromatography. Sixty-seven (67) percent of the starting monoethanolamine was converted and the product mix contained 43 weight percent ethylenediamine.

EXAMPLE 34

A ¾ inch stainless steel tube (1 ft long) was packed with a catalytic composition (66 g) comprising cobalt (50 mole percent), copper (45 mole percent) and $ZrO_2$ (5 mole percent) and was heated by a hot oil bath. The results of several runs at various temperatures are tabulated below. A mixture of monoethanolamine (MEA) and ammonia ($NH_3$:MEA mole ratio of about 7) with a blanket of hydrogen (500 psig) was pumped through the packed tube at 1,500 psig and 180 cc/hr with a Ruska ® pump. Contact time was about 10 minutes.

| | Results of Continuous Ammonolytic Operation with Co-Cu-Zr Composition | | |
|---|---|---|---|
| Run | Temp. (° C.) | Conversion (wt. %) | EDA Yield[1] (wt. %) |
| A | 150 | 32 | 82 |
| B | 175 | 78 | 70 |
| C | 200 | 82 | 40 |

[1]Ethylenediamine yield based on the weight of the product mix.

Control

Example 34 was repeated except that a commercially available catalytic composition (146 g) comprising cobalt (70–75 mole percent), copper (20–25 mole percent) and chromium oxide (1–5 mole percent) manufactured by The Harshaw Chemical Company under the designation 6-X-L649-88-3 was substituted for the catalytic composition of Example 34. The results are tabulated below.

| | Results of Continuous Ammonolytic Operation with Co-Cu-Cr Composition | | |
|---|---|---|---|
| Run | Temp. (° C.) | Conversion (wt. %) | EDA Yield[1] (wt. %) |
| A | 150 | 10 | 76 |
| B | 175 | 56 | 52 |
| C | 200 | 56 | — |

[1]Ethylenediamine yield based on the weight of the product mix.

A comparison of the data in Example 34 and the control demonstrates the superior, catalytic activity of this invention's compositions to that of a commercially available composition.

Although this invention has been described in considerable detail by the preceding examples, it is to be understood that such detail is for purposes of illustration only and is not to be construed as limitations upon the invention. Many variations can be had upon the preceding examples without departing from the spirit and scope of the appended claims.

What is claimed is:

1. In a method of preparing amines, the method comprising contacting at reactive conditions at least one alcohol, aldehyde or ketone, or a mixture thereof, with an aminating agent in the presence of a catalyst, the improvement wherein the catalyst comprises, calculated in mole percent and on an oxide-free basis, about:
   (1) 20 to about 90 percent cobalt;
   (2) 8 to about 72 percent copper; and
   (3) 1 to about 16 percent of a third component selected from the group consisting of iron, zinc, zirconium and mixtures thereof.

2. The method of claim 1 wherein the catalyst comprises, calculated in mole percent and on an oxidefree basis, about:
   (1) 30 to about 80 percent cobalt;
   (2) 15 to about 60 percent copper; and
   (3) 2 to about 14 percent of a third component selected from the group consisting of iron, zinc, zirconium and mixtures thereof.

3. The method of claim 1 wherein the catalyst comprises calculated in mole percent and on an oxide-free basis, about:
   (1) 40 to about 70 percent cobalt;
   (2) 20 to about 50 percent copper; and
   (3) 4 to about 10 percent of a third component selected from the group consisting of iron, zinc, zirconium and mixtures thereof.

4. The method of claim 1 wherein the third component is only iron, only zinc or only zirconium.

5. The method of claim 1 wherein the third component is only zirconium.

6. The method of claim 1 wherein the contacting is performed at a temperature of at least about 75° C. and a pressure of at least about 1,000 psi.

7. In a method for preparing amines, the method comprising contacting at reactive conditions at least one alcohol with an aminating agent in the presence of a catalyst, the improvement wherein the catalyst comprises, calculated in mole percent and on an oxide-free basis, about:
   (1) 20 to about 90 percent cobalt;
   (2) 8 to about 72 percent copper; and
   (3) 1 to about 16 percent of a third component selected from the group consisting of iron, zinc, zirconium and mixtures thereof.

8. The method of claim 7 wherein the catalyst comprises, calculated in mole percent and on an oxidefree basis, about:
   (1) 30 to about 80 percent cobalt;
   (2) 15 to about 60 percent copper; and
   (3) 2 to about 14 percent of a third component selected from the group consisting of iron, zinc, zirconium and mixtures thereof.

9. The method of claim 7 wherein the catalyst comprises, calculated in mole percent and on an oxide-free basis, about:
   (1) 40 to about 70 percent cobalt;
   (2) 20 to about 50 percent copper; and
   (3) 4 to about 10 percent of a third component selected from the group consisting of iron, zinc, zirconium and mixtures thereof.

10. The method of claim 7 wherein the third component is only iron, only zinc or only zirconium.

11. The method of claim 7 wherein the third component is only zirconium.

12. The method of claim 7 wherein the contacting is performed at a temperature of at least about 75° C. and a pressure of at least about 1,000 psi.

13. In a method for preparing amines, the method comprising contacting at reactive conditions at least one aldehyde or ketone or a mixture thereof with an aminating agent in the presence of a catalyst, the improvement wherein the catalyst comprises, calculated in mole percent and on an oxide-free basis, about:
   (1) 20 to about 90 percent cobalt;
   (2) 8 to about 72 percent copper; and (3) 1 to about 16 percent of a third component selected from the group consisting of iron, zinc, zirconium and mixtures thereof.

14. The method of claim 13 wherein the catalyst comprises, calculated in mole percent and on an oxide-free basis, about:
(1) 30 to about 80 percent cobalt;
(2) 15 to about 60 percent copper; and
(3) 2 to about 14 percent of a third component selected from the group consisting of iron, zinc, zirconium and mixtures thereof.

15. The method of claim 13 wherein the catalyst comprises, calculated in mole percent and on an oxide-free basis, about:
(1) 40 to about 70 percent cobalt;
(2) 20 to about 50 percent copper; and
(3) 4 to about 10 percent of a third component selected from the group consisting of iron, zinc, zirconium and mixtures thereof.

16. The method of claim 13 wherein the third component is only iron, only zinc or only zirconium.

17. The method of claim 13 wherein the third component is only zirconium.

18. The process of claim 13 wherein the contacting is performed at a temperature of at least about 75° C. and a pressure of at least about 1,000 psi.

19. A catalyst for preparing amines from at least one alcohol, aldehyde or ketone, or a mixture thereof, the catalyst comprising, calculated in mole percent and on an oxide-free basis, about:
(1) 20 to about 90 percent cobalt;
(2) 8 to about 72 percent copper; and
(3) 1 to about 16 percent of a third component selected from the group consisting of iron, zinc, zirconium and mixtures thereof.

20. The catalyst of claim 19 comprising about:
(1) 30 to about 80 percent cobalt;
(2) 15 to about 60 percent copper; and
(3) 2 to about 14 percent of a third component selected from the group consisting of iron, zinc, zirconium and mixtures thereof.

21. The catalyst of claim 19 comprising about:
(1) 40 to about 70 percent cobalt;
(2) 20 to about 50 percent copper; and
(3) 4 to about 10 percent of a third component selected from the group consisting of iron, zinc, zirconium and mixtures thereof.

22. The catalyst of claim 19 wherein the third component is only iron, only zinc or only zirconium.

23. The catalyst of claim 19 wherein the third component is only zirconium.

* * * * *